US00PP36083P2

(12) United States Plant Patent
Hansen

(10) Patent No.: US PP36,083 P2
(45) Date of Patent: Aug. 27, 2024

(54) ***BAPTISIA* PLANT NAMED 'Grape Escape'**

(50) Latin Name: ***Baptisia* hybrid**
Varietal Denomination: Grape Escape

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,758

(22) Filed: Jan. 22, 2024

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP26,587 P2 * 4/2016 Hansen ..... A01H 5/02
Plt./263.1

* cited by examiner

*Primary Examiner* — Karen M Redden

(57) ABSTRACT

A new and distinct plant cultivar of hardy herbaceous False Indigo plant named *Baptisia* 'Grape Escape' is characterized by flowers that open up deep purplish-red with a light cream-colored keel beginning in late May and continuing for three weeks. The new plant has a narrow, medium height, upright, vase-shaped, multi-stemmed, winter-hardy habit with glaucous dark-green tri-foliate foliage and is suitable for landscaping as a specimen or en masse.

2 Drawing Sheets

Botanical classification: *Baptisia* hybrid.
Cultivar designation: 'Grape Escape'.

STATEMENT REGARDING PRIOR DISCLOSURES UNDER 37 CFR 1.77(b)(6)

*Baptisia* 'Grape Escape' was first promoted with a brief description and photographs on a website operated by Walters Gardens, Inc. on Feb. 1, 2023, followed by the "Walters Gardens 23-24 Catalog" initially distributed by Walters Gardens, Inc. on May 19, 2023. The first private sale of *Baptisia* 'Grape Escape' was made by Walters Gardens, Inc. on Jan. 23, 2023, to Edwards Greenhouse and Flowershop. Information and plants for this sale and all sales thereafter were obtained from the inventor. No plants of *Baptisia* 'Grape Escape' have been sold or offered for sale, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Grape Escape', and will be referred to hereafter by its cultivar name, 'Grape Escape', and the new plant. The new plant represents a new false indigo, a hardy herbaceous perennial grown for landscape and cut flower use.

'Grape Escape' arose from an ongoing breeding program of the inventor at a wholesale perennial nursery in Zeeland, Michigan with the specific intention of improving garden worthiness of perennial false indigo plants with a wider variety of flower colors and improved garden habit.

*Baptisia* 'Grape Escape' was a single seedling selection from a cross between a 'Pink Truffles' U.S. Plant Pat. No. 26,588 as the female or seed parent times 'Blue Towers' U.S. Plant Pat. No. 27,088 as the male or pollen parent. The cross was performed at the same nursery in Zeeland, Michigan with the seeds collected on Jul. 15, 2015. The seeds were then sown at the same nursery in Zeeland, Michigan in the spring of 2016. The initial selection was made in the spring of 2017 at the same nursery in Zeeland and later given the breeder code 15-12-2.

'Grape Escape' was initially asexually propagated by stem cuttings at a wholesale perennial nursery in Zeeland, Michigan in 2018. The resultant plants have demonstrated that the new plant has remained stable and true to type in successive generations of asexual propagation.

The nearest comparison plants known to the inventor are: 'Grape Taffy' U.S. Plant Pat. No. 26,587, 'Violet Dusk' U.S. Plant Pat. No. 32,553, 'Burgundy Blast' U.S. Plant Pat. No. 34,689, and 'Plum Rosy' (not patented).

'Grape Taffy' is shorter and more compact in habit with fewer flowers that are a lighter reddish-purple with a buff-yellow keel. 'Violet Dusk' is a similar habit with shorter inflorescences and the flowers are lavender-violet with cream-colored keels. 'Burgundy Blast' has a slightly smaller habit with shorter inflorescences and the flowers are deep wine red without the contrasting ream-colored keel. 'Plum Rosy' has a smaller habit and flowers that open mauve pink and turn to a near white with age.

The female parent has clear soft-pink flowers on a slightly taller plant. The male parent has a taller habit, and the flowers are dark purplish-blue.

The new plant differs from all *Baptisia* known to the inventor in the following combined traits:

1. Flowers open deep purplish-red with a light creamy-colored keel and retain their color through the effective season;
2. Flowering begins in late May in Michigan and continues for about three weeks;
3. Medium-height, upright, vase-shaped, multi-stemmed, winter-hardy habit;
4. Glaucous, dark-green, tri-foliate foliage.

BRIEF DESCRIPTION OF THE DRAWINGS

The photographs of 'Grape Escape' demonstrate the unique traits and the overall appearance of the new plant. The colors are as accurate as reasonably possible with color reproductions. Variations in ambient light spectrum, source, and direction may cause the appearance of minor variation in color. The accompanying photograph is of a five-year-old plant growing in an open full-sun trial garden in Zeeland, Michigan.

DETAILED BOTANICAL DESCRIPTION OF THE PLANT

Figure 1:
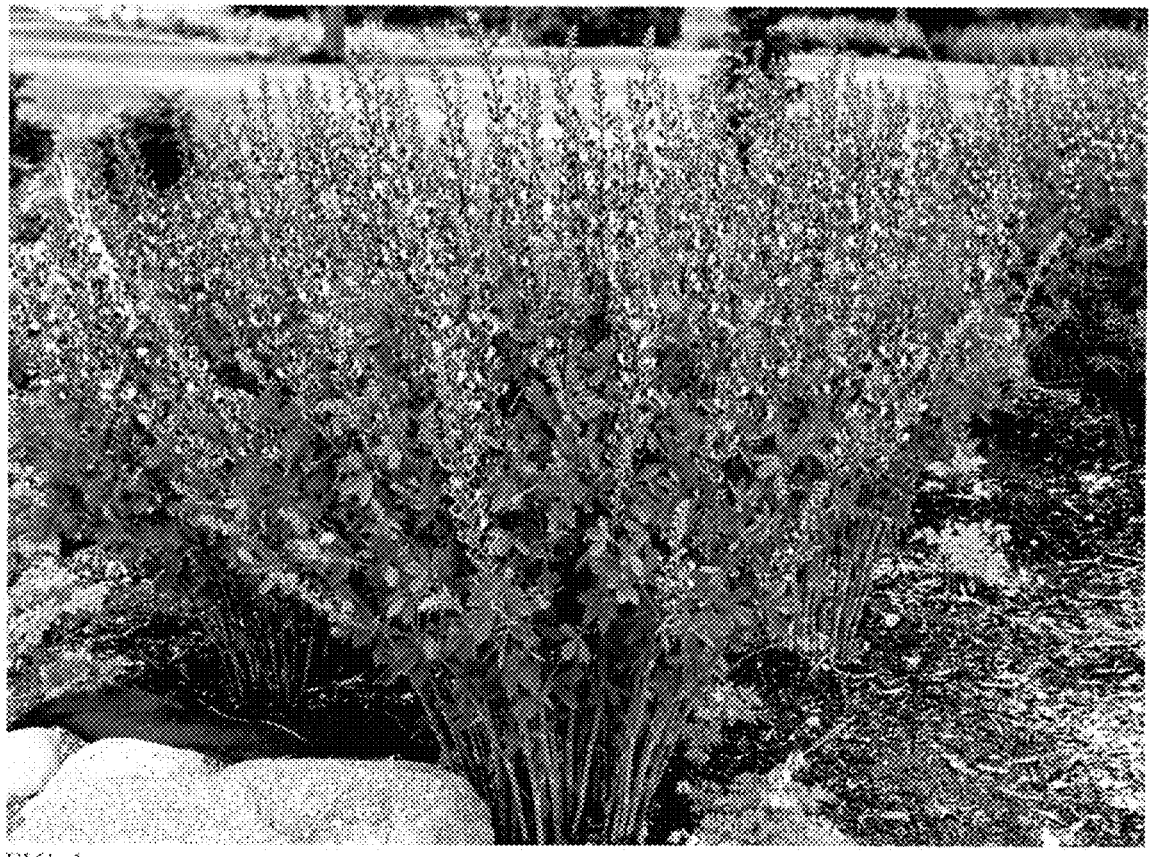
FIG. 1 shows the habit of a plant in full flower.
Figure 2:
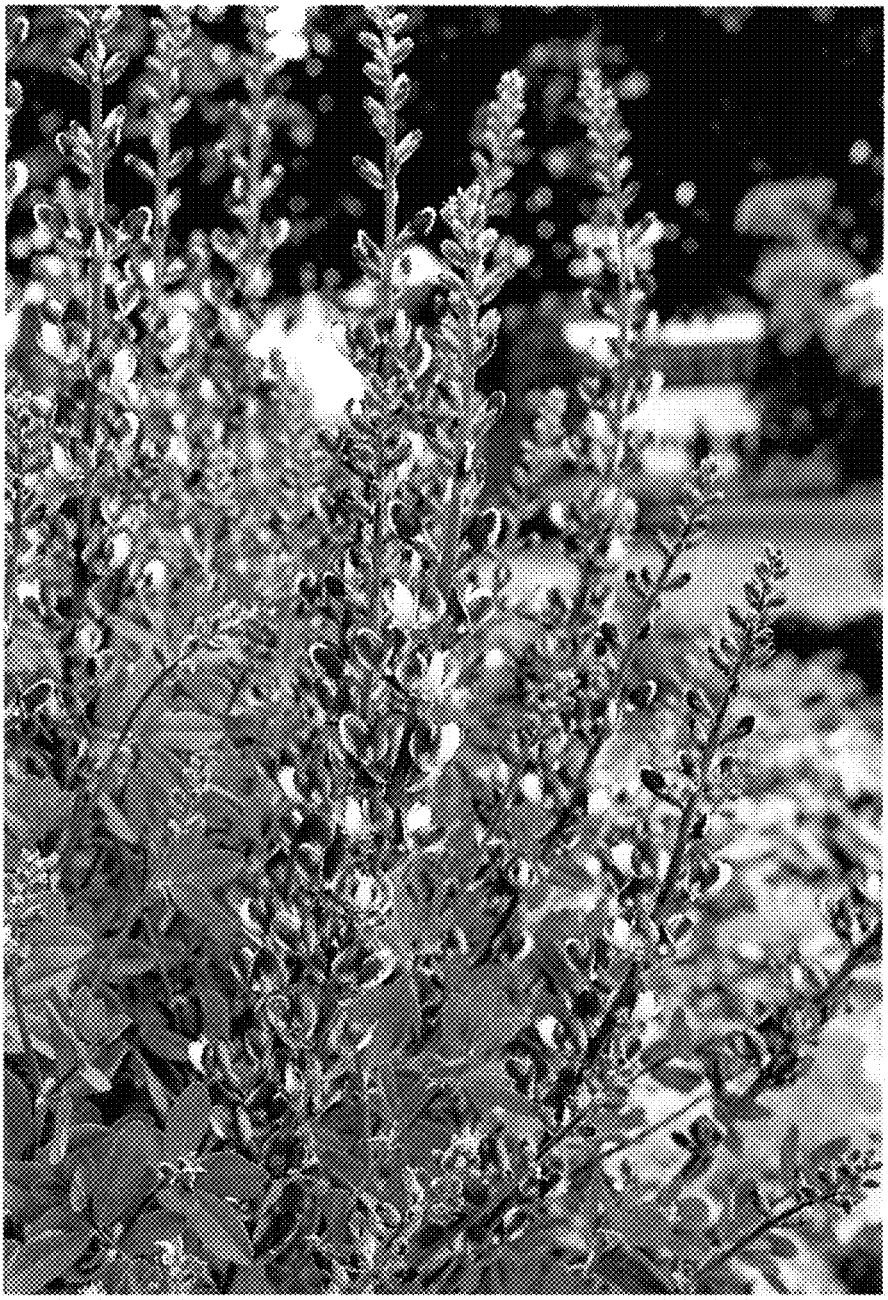
FIG. 2 shows a close-up of the inflorescence.

The following is a detailed description of a five-year-old plant of 'Grape Escape' as grown outdoors in a trial block at a wholesale perennial nursery in Zeeland, Michigan. Plants of the new cultivar have not been tested under all possible conditions. The phenotype may vary with changes in the environment, climate, and cultural conditions without any change, however, in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage.

Plant size: Stems and crown about 28 cm across at soil level, at flowering about 120 cm tall from soil to top of flowers and 130 cm wide just below initial flowers.

Roots: Fibrous, well-branched, long, deeply rooted.

Root color: Nearest RHS 161D.

Propagation method: Stem cuttings, rooting in about three weeks.

Growth rate: Moderate to average.

Stems: Rigid and upright; highly glaucous; glabrous; cylindrical with shallow longitudinal furrows; lower two to three nodes without leaves or branches; normally two to five branches per plant below flowers; about 60 stems per clump.

Stem size: Main stem to about 9 mm diameter at the base and 105 cm tall, average about 100 cm long and about 8 mm diameter; to about 98 cm long from soil to below initial flowers.

Stem branches: Primary branches at 45 to 60-degree angle above horizontal, up to 28 cm long and 5 mm diameter, average for primary branches about 24 cm long and 4 mm diameter, smaller distally; and two to three alternate secondary branches per stem of about 10 cm long and 3 mm diameter, averaging about 7.5 cm long and 2.5 mm diameter.

Stem color: Variable, between RHS N187B and RHS N187C, and between RHS 138A and RHS 194B.

Stem scales: At stem nodes; lanceolate; emarginate to retuse apex; truncate clasping base; margin entire; dehiscing to leave behind a thin scar on stem; about 30 mm long, 18 mm wide at the base and 21 mm wide in the center.

Stem scale color: Variable, nearest RHS N186B distally, nearest RHS 138B proximally, and between RHS 146B and RHS 147B before dehiscing.

Internodes: Variable; between 1.2 to 15 cm apart between lowest branches, average about 9 cm.

Internode color: Between RHS 145B and RHS 145C.

Foliage: Alternate; ternate to palmately compound with three leaflets; outer two leaflets independent, at about 90-degree angle to middle leaflet; up to 6.4 cm long and 10 cm wide.

Leaflet: Three; oblanceolate; apex rounded emarginate; base cuneate; margins entire; petiolate; adaxial and abaxial surfaces matte, glabrous, slightly glaucous adaxial and abaxial; middle lobe to about 5.3 cm long and 2 cm wide, side lobes about 5 cm long and 1.9 cm wide.

Leaflet color: Newly expanding adaxial nearest RHS 137A, abaxial nearest RHS 137B; mature adaxial nearest RHS NN137B, abaxial between RHS NN137C and RHS 189A.

Venation: Pinnate, glabrous, thin, not conspicuous adaxial.

Vein color: Expanding foliage adaxial midrib nearest RHS 146A and secondary veins nearest RHS 146C, abaxial expanding foliage midrib nearest RHS 146C and secondary veins nearest RHS 137B; mature adaxial midrib nearest RHS 146A and secondary veins between RHS 137A and RHS 137B, abaxial midrib lighter than RHS 145D and secondary veins nearest RHS NN137A abaxial.

Petioles: Glabrous; slightly glaucous; concavo-convex; to about 9 mm long and 2 mm wide at the base, average about 6 cm long and 1.5 mm wide.

Petiole color: Adaxial center between RHS 147C and 146D and edges RHS 138A, abaxial between RHS 138A and RHS 146C.

Stipules: Narrowly lanceolate, acute apex with base truncate; to about 31 mm long and 9 mm wide, average 22 mm long and 7 mm wide with largest stipules below primary branches and decreasing distally and on secondary branches.

Stipule color: Nearest RHS 138A on both adaxial and abaxial.

Peduncle: Cylindrical with vertical shallow ridges and furrows; glaucous; glabrous; from first flower to apex about 30 cm long; diameter at the base of first flower about 4 mm and about 2 mm diameter at the apex.

Peduncle color: Between RHS N187A and RHS N186B in the flowering portions.

Pedicel: Cylindrical, glabrous, glaucous; about 6 mm long and 1 mm diameter.

Pedicel color: Between RHS N189A and RHS N186B.

Calyx: Campanulate; four-lobed; to about 9 mm long, 7 mm tall, and 7 mm across at apex.

Sepals: Four; one larger dorsal, one ventral, and two lateral; dorsal sepal apex emarginate, notched about 1 mm deep with lobes acute; other three sepals with acute apices; fused into tube in proximal 6 mm; margin entire; glabrous adaxial and abaxial; glaucous adaxial and matte abaxial; dorsal sepal to about 9 mm long and 6 mm wide at fusion; other three sepals to about 9 mm long and 3 mm across at fusion.

Sepal color: Adaxial ventral portion nearest RHS 145A, lateral and dorsal portions nearest RHS 146C with a light blush of nearest RHS N186B; abaxial lateral and dorsal portions between RHS N189A and RHS N186B, ventral portion nearest RHS 146D.

Buds one day prior to anthesis: Oblong-elliptic, slightly flatted vertically; to about 23 mm long and 10 mm tall, and 9 mm wide, slightly smaller in distal flowers.

Bud color: One day prior to opening exposed keel petal nearest RHS 1D, enfolded banner petal proximally nearest RHS N186B and distally nearest RHS 79A, exposed alae petals nearest RHS 79A.

Flower: Zygomorphic; papilionaceous; non-secund; held at about 45-degree to 60-angle above horizontal; about 40 flowers per main center panicle and about 15 per secondary branch; seasonally effective for about 3 weeks beginning in late May in Zeeland, MI; individual flowers remain effective and on raceme for about four days; individually to about 23 mm long, 15 mm tall and 19 mm wide at largest portions; consisting of an upper banner, a lower keel made up of two lobes folded around gynoecium and androecium; and two lateral wings or alae laterally appressed against keel.

Flower fragrance: None detected.

Petals: Five; with a lower fused keel, an upper banner, and two lateral wings or alae; keel comprised of two sections that are folded around stamens and pistil.

*Banner petal.*—Conduplicate, reflexed upward and backward and pinched in the middle; apex retuse, with rounded emarginate apex notched about 1 mm deep; base claw-like, margin entire; to about 18 mm long, 19 mm across natural width, 20 mm wide flattened spread and 7 mm tall; basal portion attenuate claw-like, 5 mm long and 3 mm wide.

*Banner color.*—Adaxial toward center nearest RHS N186B, lightening toward margins to between RHS N79B and RHS N79A with claw base nearest RHS 145A; abaxial between RHS N79A and RHS N79B, with claw nearest RHS 145A.

*Keel.*—Comprised of two main lobes that are folded around stamens and pistil; fused in the distal one-third with the two lobes having rounded apices and the bases separate and claw-like, and a small basal lobe about 2 mm long and 2 mm wide above each claw pointing toward base; margin entire; each main lobe about 21 mm long and 9 mm across in middle; blade portion to about 16 mm long and 9 mm tall; with claw to about 6 mm long and base narrowed to 1.5 mm wide in the proximal 2 mm.

*Keel color.*—Adaxial and abaxial claw nearest RHS 145D; adaxial 3 mm and abaxial distal 4 mm to 5 mm of the blade between RHS 79A and RHS N186B, adaxial middle and proximal portion nearest RHS 145D.

*Alae.*—Two; papilionaceous corolla appendage with rounded apex, claw-like base, and entire margin; with 2 mm long by 2 mm wide lobe pointing toward base and about one-third of the way from base; about 20 mm long and 7 mm tall, with the claw to 2 mm wide at base of the blade and 1.5 mm wide at the base, and 6 mm long; blade about 15 mm long and 7 mm wide.

*Alae color.*—Adaxial and abaxial claw nearest RHS 145C; adaxial and abaxial lobe and basal 2 mm of blade nearest RHS 145D; adaxial main blade portion nearest RHS 157D with a light blush of nearest RHS N186B, and distal margin nearest RHS N186B; abaxial main lobe portion between RHS N186B and RHS N79A.

Receptacle: Disk-shaped, about 4 mm diameter and 2 mm depth.

Receptacle color: Lateral and dorsal portions between RHS N189A and RHS N186B, ventral portion nearest RHS 146D.

Gynoecium: One, with superior ovary and stipe; to about 21 mm long.

*Style.*—Cylindrical; glabrous; slightly lustrous; tapered and curved near stigma, about 6 mm long and about 0.7 mm diameter above ovary; color between RHS 149D and RHS 145D with a light blush distally of nearest RHS N186B.

*Stigma.*—About 0.2 mm diameter; color nearest RHS 150D.

*Ovary.*—Superior above hypanthium; suspended by stipe; about 8 mm long and about 2 mm in diameter; color between RHS 144A and RHS 143C.

*Stipe.*—Cylindrical; glabrous; slightly lustrous; about 4 mm long and 0.7 mm diameter; color between RHS 145A and RHS N144C.

Androecium:

*Stamens.*—Ten.

*Filament.*—Glabrous; slightly lustrous; not united; to 21 mm in length and about 1 mm in diameter; slightly curved upward distally; color nearest RHS 149D.

*Anther.*—Dorsifixed; oblong; about 2 mm long and 1.2 mm wide; color nearest RHS 17B; Pollen; spherical; abundant; color nearest RHS 17A.

Fruit: Bivalve inflated ellipsoidal pod; glabrous; about 32 mm long, 18 mm across and 13 mm thick; with thin, linear, arcuate, terminal beak about 3 mm long and about 1 mm thick; rounded base.

Fruit color: At maturity between 200A and RHS 202A.

Seeds: About 8 per pod (open pollinated); reniform; glabrous; about 4 mm long, 3 mm across, and 2 mm thick; color nearest RHS N199C.

Hardiness: To USDA zones 4 to 9; tolerant of heavy clay or light loamy-sand soils; able to withstand drought conditions once established.

Diseases: Susceptibility or resistance to diseases beyond that typically found in other false indigo plants has not been observed.

It is claimed:

1. A new and distinct cultivar of *Baptisia* plant named 'Grape Escape' as herein described and illustrated.

* * * * *